United States Patent

Kojima et al.

[11] 4,103,030
[45] Jul. 25, 1978

[54] NOVEL CYCLOPROPYLMETHYLAMINE DERIVATIVES

[75] Inventors: Atsuyuki Kojima, Nishinomiya; Yoshito Kameno, Minoo; Junki Katsube, Toyonaka; Shigeho Inaba, Takarazuka; Hisao Yamamoto, Kobe, all of Japan

[73] Assignee: Sumitomo Chemical Company, Limited, Japan

[21] Appl. No.: 635,331

[22] Filed: Nov. 26, 1975

[30] Foreign Application Priority Data

Dec. 11, 1974 [JP] Japan .................. 49-142899
May 16, 1975 [JP] Japan .................. 50-58929

[51] Int. Cl.² .............. A01N 9/20; A01N 9/24; C07C 91/16; C07C 91/28
[52] U.S. Cl. .............. 424/330; 260/570.5 CA
[58] Field of Search .............. 424/330; 260/570.5 CA

[56] References Cited

U.S. PATENT DOCUMENTS 3,941,833  3/1976  Gognaco ............ 260/570.5 CA

FOREIGN PATENT DOCUMENTS 948,730   2/1964  United Kingdom .......... 260/570.5
1,086,191 10/1967 United Kingdom .......... 260/570.5

OTHER PUBLICATIONS

J. Org. Chem. U.S.S.R.-5p178 (1969), Bolesov et al., New Rearrangement of 2,2'-(cyclopropylimino)diethanols.
Chem. Abst., 68(1) 243 (1968) - Teotino et al.

*Primary Examiner*—Albert T. Meyers
*Assistant Examiner*—D. W. Robinson
*Attorney, Agent, or Firm*—Birch, Stewart, Kolasch and Birch

[57] ABSTRACT

Novel cyclopropylmethylamine compounds of the formula:

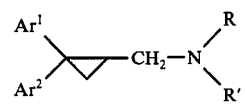

wherein $Ar^1$ represents a phenyl group having one or more substituents selected from the group consisting of halogen, $C_1$-$C_4$ alkyl, $C_1$-$C_4$ alkoxy and trifluoromethyl, of which at least one is present at the o- or m-position, $Ar^2$ represents an unsubstituted phenyl group or a phenyl group substituted with one or more substituents selected from the group consisting of halogen and $C_1$-$C_4$ alkyl, R represents hydrogen, $C_1$-$C_4$ alkyl or $C_2$-$C_4$ hydroxyalkyl and R' represents $C_1$-$C_4$ alkyl or $C_2$-$C_4$ hydroxyalkyl, and their non-toxic salts, which possess various useful pharmacological activities and can be produced by reduction of the corresponding compounds of the formula:

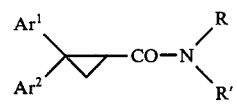

wherein $Ar^1$, $Ar^2$, R and R' are each as defined above or by condensation of the corresponding compounds of the formula:

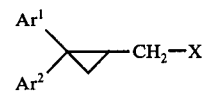

wherein $Ar^1$ and $Ar^2$ are each as defined above and X is a conventional leaving (removable) group with amines of the formula:

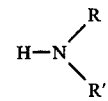

wherein R and R' are each as defined above.

6 Claims, No Drawings

NOVEL CYCLOPROPYLMETHYLAMINE DERIVATIVES

The present invention relates to novel cyclopropylmethylamine derivatives, and their production and use.

The novel cyclopropylmethylamine derivatives provided by this invention are cyclopropylmethylamine compounds of the formula:

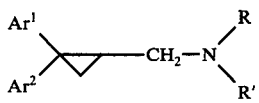

wherein $Ar^1$ represents a phenyl group having one or more substituents selected from the group consisting of halogen, $C_1$–$C_4$ alkyl, $C_1$–$C_4$ alkoxy and trifluoromethyl, of which at least one is present at the o- or m-position, $Ar^2$ represents an unsubstituted phenyl group or a phenyl group substituted with one or more substituents selected from the group consisting of halogen and $C_1$–$C_4$ alkyl, R represents hydrogen, $C_1$–$C_4$ alkyl or $C_2$–$C_4$ hydroxyalkyl and R' represents $C_1$–$C_4$ alkyl or $C_2$–$C_4$ hydroxyalkyl, and their non-toxic salts.

In the above significances, the term "halogen" is intended to mean chlorine, bromine, fluorine, etc. As "$C_1$–$C_4$ alkyl," there are exemplified methyl, ethyl, isopropyl, isobutyl, etc. Examples of "$C_{1-C4}$ alkoxy" include methoxy, ethoxy, propoxy, etc. Examples of "$C_2$–$C_4$ hydroxyalkyl" are hydroxyethyl, hydroxypropyl, hydroxybutyl, etc.

Among the cyclopropylmethylamine compounds [I] of the invention, those of the following formula are preferable:

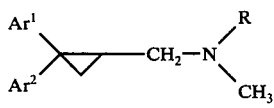

wherein $Ar^1$, $Ar^2$ and R are each as defined above.

Specific examples of such cyclopropylmethylamine compounds [I] are as follows:

N,N-Dimethyl-2-(m-chlorophenyl)-2-phenylcyclopropylmethylamine;
N,N-Dimethyl-2-(o-chlorophenyl)-2-phenylcyclopropylmethylamine;
N,N-Dimethyl-2-(m-methylphenyl)-2-phenylcyclopropylmethylamine;
N,N-Dimethyl-2-(o-methylphenyl)-2-phenylcyclopropylmethylamine;
N,N-Dimethyl-2-(m-bromophenyl)-2-phenylcyclopropylmethylamine;
N,N-Dimethyl-2-(o-bromophenyl)-2-phenylcyclopropylmethylamine;
N,N-Dimethyl-2-(m-trifluoromethylphenyl)-2-phenylcyclopropylmethylamine;
N,N-Dimethyl-2-(o-trifluoromethylphenyl)-2-phenylcyclopropylmethylamine;
N,N-Dimethyl-2-(m-methoxyphenyl)-2-phenylcyclopropylmethylamine;
N,N-Dimethyl-2-(o-methoxyphenyl)-2-phenylcyclopropylmethylamine;
N-Methyl-2-(m-chlorophenyl)-2-phenylcyclopropylmethylamine;
N-Methyl-2-(o-chlorophenyl)-2-phenylcyclopropylmethylamine;
N-Methyl-2-(m-methylphenyl)-2-phenylcyclopropylmethylamine;
N-Methyl-2-(o-methylphenyl)-2-phenylcyclopropylmethylamine;
N-Methyl-2-(m-bromophenyl)-2-phenylcyclopropylmethylamine;
N-Methyl-2-(o-bromophenyl)-2-phenylcyclopropylmethylamine;
N-Methyl-2-(m-trifluoromethylphenyl)-2-phenylcyclopropylmethylamine;
N-Methyl-2-(o-trifluoromethylphenyl)-2-phenylcyclopropylmethylamine;
N-Methyl-2-(m-methoxyphenyl)-2-phenylcyclopropylmethylamine;
N-Methyl-2-(o-methoxyphenyl)-2-phenylcyclopropylmethylamine;
N,N-Dimethyl-2-(3,5-dichlorophenyl)-2-phenylcyclopropylmethylamine;
N,N-Dimethyl-2,2-di(m-chlorophenyl)cyclopropylmethylamine;
N-Methyl-2,2-di(m-chlorophenyl)cyclopropylmethylamine;
N-Methyl-N-(3-hydroxypropyl)-2-(m-chlorophenyl)-2-phenylcyclopropylmethylamine;
N-Methyl-N-(3-hydroxypropyl)-2-(o-chlorophenyl)-2-phenylcyclopropylmethylamine;
N-Methyl-N-(3-hydroxypropyl)-2-(m-methoxyphenyl)-2-phenylcyclopropylmethylamine;
N-Methyl-N-(2-hydroxyethyl)-2-(m-chlorophenyl)-2-phenylcyclopropylmethylamine;
N-Methyl-N-(2-hydroxyethyl)-2-(o-chlorophenyl)-2-phenylcyclopropylmethylamine;
N-Methyl-N-(2-hydroxyethyl)-2-(m-methoxyphenyl)-2-phenylcyclopropylmethylamine;
N-Methyl-N-(2-hydroxyethyl)-2-(m-trifluoromethylphenyl)-2-phenylcyclopropylmethylamine;
N-Methyl-N-(2-hydroxyethyl)-2,2-di(m-chlorophenyl)-cyclopropylmethylamine, etc.

The cyclopropylmethylamine compounds [I] can form acid-addition salts (e.g. hydrochloride, hydrobromide, sulfate, acetate, oxalate, citrate, tartrate, succinate, fumarate, lactate) and quaternary ammonium salts (e.g. methochloride, methiodide).

The cyclopropylmethylamine compounds [I] and their non-toxic salts exhibit various pharmacological properties and are useful as medicines. That is, these compounds antagonize the central nervous system depressant effects of tetrabenazine and reserpine, and moreover possess a mood-elevating activity. Therefore, they may be useful as antidepressants and/or anorexics.

The cyclopropylmethylamine compounds [I] and their pharmaceutically acceptable salts can be administered parenterally or orally (with dosage adjusted to individual requirements) in the form of conventional pharmaceutical preparations. For instance, they can be administered in the form of conventional solid pharmaceutical preparations such as tablets or capsules, or in the form of conventional liquid pharmaceutical preparations such as suspensions, emulsions or solutions.

The cyclopropylmethylamine compounds [I] of the invention can be prepared from the corresponding compounds of the formula:

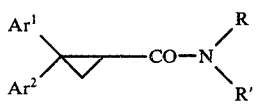   [II]

wherein Ar¹, Ar², R and R' are each as defined above by subjecting the latter to reduction. A reducing agent such as an alkali metal in an alcoholic solvent, a metal hydride or the like may be preferably employed for achievement of the reduction. An electrolytic reduction can also be used for the same purpose.

It is especially preferable to use a metal hydride such as lithium aluminum hydride, sodium aluminum diethyl dihydride or sodium bis(2-methoxyethoxy)aluminum hydride in an inert organic solvent such as diethyl ether, diisopropyl ether, tetrahydrofuran, dioxane, ethylene glycol dimethyl ether, heptane, hexane, cyclohexane, benzene or toluene. The temperature for the treatment in this case may be varied from ice-cooling to the refluxing temperature of the reduction system.

Sodium borohydride is another example of practically utilizable reducing agents, particularly when used in the presence of a salt such as aluminum chloride or on activation of the carboxamide group in the compound [II] with triethyloxonium fluoroborate or the like. Diborane is a further example of an efficient reducing agent.

The cyclopropylmethylamine compounds [I] can be also prepared by reacting the corresponding compounds of the formula:

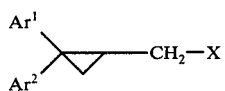   [III]

wherein Ar¹ and Ar² are each as defined above and X is a conventional leaving (removable) group such as halogen (e.g. chlorine, bromine) or sulfonyloxy (e.g. methanesulfonyloxy, p-toluene-sulfonyloxy) with amines of the formuala:

   [IV]

wherein R and R' are each as defined above in an inert organic solvent such as diethyl ether, diisopropyl ether, tetrahydrofuran, dioxane, ethylene glycol dimethyl ether, ethanol, methanol, benzene, toluene or pyridine in the presence or absence of an acid binding agent. Examples of the acid binding agent are pyridine, picoline, triethylamine, dimethylaniline, etc. The temperature for the reaction may be varied from ice-cooling to the refluxing temperature of the reaction system.

The cyclopropylmethylamine compounds [I] thus produced may be separated from the reaction mixture and purified by conventional procedures.

The obtained cyclopropylmethylamine compounds [I] may be converted into their salts in a conventional manner, and reconversion from the salts to the original free bases may be also carried out in a conventional manner.

The starting materials used in this invention are novel and can be produced according to the following scheme:

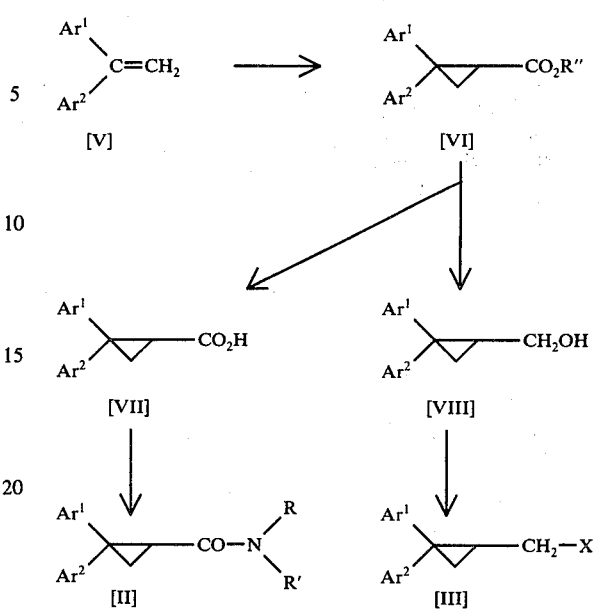

wherein Ar¹, Ar², R, R' and X are each as defined above and R" represents $C_1$-$C_4$ alkyl.

That is, the olefins [V] are reacted with alkoxycarbonyl carbenes, prepared from alkyl diazoacetates, to afford the alkyl cyclopropanecarboxylates [VI]. The compounds [VI] are saponified to the corresponding cyclopropane carboxylic acids [VII], which are then converted into their active acyl derivatives such as acid anhydrides or acid halides and reacted with amines to afford the starting compounds [II]. Alternatively, the compounds [VI] may be reduced to the corresponding cyclopropylmethyl alcohols [VIII], followed by active esterification to afford the starting compounds [III].

The following examples are given for the purpose of illustration only, and it is not intended to limit the invention thereto.

EXAMPLE 1

To a solution of lithium aluminum hydride (0.30 g) in ether (10 ml) was added a solution of 2-(m-chlorophenyl)-2-phenylcyclopropanecarboxylic acid N,N-dimethylamide (0.900 g) in ether (15 ml) under ice-cooling, and the resulting mixture was stirred under reflux for 3 hours. The reaction mixture was cooled, admixed with a 10% aqueous solution of sodium hydroxide (20 ml) and extracted with ether. The ether extract was dried over anhydrous magnesium sulfate and evaporated to afford N,N-dimethyl-2-(m-chlorophenyl)-2-phenylcyclopropylmethylamine as an oily substance. M.P. 188° – 190° C (hydrochloride).

EXAMPLE 2

To a solution of 2-methylaminoethanol (0.29 g) in ethanol (5 ml) was added a solution of 2,2-di(m-chlorophenyl)cyclopropylmethyl chloride (0.40 g) in ethanol (10 ml) at room temperature, and stirring was carried out under reflux for 10 hours. The reaction mixture was evaporated and poured into a 10% aqueous solution of sodium hydroxide. The chloroform extract was dried and chromatographed to afford N-methyl-N-(2-hydroxyethyl)-2,2-di(m-chlorophenyl)-cyclopropylmethylamine as an oily substance. M.P. 152° – 154° C (hydrochoride).

In the same manner as above, the following compounds were obtained:

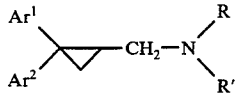

| Ar¹ | Ar² | R | R' | M.P. (° C) | salt/base |
|---|---|---|---|---|---|
| 3-Cl—C₆H₄ | C₆H₅ | CH₃ | CH₃ | 189–190 | HCl |
| 2-Cl—C₆H₄ | C₆H₅ | CH₃ | CH₃ | 232–233 | HCl |
| 2-CH₃—C₆H₄ | C₆H₅ | CH₃ | CH₃ | 231–232 | HCl |
| 2-Cl—C₆H₄ | C₆H₅ | H | CH₃ | 244–245 | HCl |
| 3-CH₃—C₆H₄ | C₆H₅ | CH₃ | CH₃ | 201–202 | HCl |
| 3-Br—C₆H₄ | C₆H₅ | CH₃ | CH₃ | 162–164 | HCl |
| 3-CF₃—C₆H₄ | C₆H₅ | CH₃ | CH₃ | 140–142 | HCl |
| 3-CH₃O—C₆H₄ | C₆H₅ | CH₃ | CH₃ | 164–165 | HCl |
| 3-Cl—C₆H₄ | C₆H₅ | H | CH₃ | 224–225 | HCl |
| 3,5-di-Cl—C₆H₃ | C₆H₅ | CH₃ | CH₃ | 165–166 | HCl |
| 3-Cl—C₆H₄ | 3-CH₃—C₆H₄ | CH₃ | CH₃ | 153–154 | HCl |
| 3-Cl—C₆H₄ | 3-Cl—C₆H₄ | CH₃ | CH₃ | 149–151 | HCl |
| 3-Cl—C₆H₄ | C₆H₅ | (CH₂)₃OH | CH₃ | oily | base¹⁾ |
| 2-Cl—C₆H₄ | C₆H₅ | CH₃ | (CH₂)₃OH | oily | base²⁾ |
| 3-Cl—C₆H₄ | 3-Cl—C₆H₄ | CH₃ | (CH₂)₂OH | 152–154 | HCl |
| 3-CH₃O—C₆H₄ | C₆H₅ | (CH₂)₂OH | CH₃ | oily | base³⁾ |
| 3-Cl—C₆H₄ | 3-CH₃—C₆H₄ | H | (CH₂)₂OH | 183–185 | HCl |
| 3-CH₃O—C₆H₄ | C₆H₅ | (CH₂)₂OH | (CH₂)₂OH | oily | base⁴⁾ |

Note:
¹⁾I.R. (neat): 3350 (br), 3060, 3020, 2940, 1595, 1565, 1480, 1075 and 700 cm⁻¹.
²⁾I.R. (neat): 3400 (br), 3055, 3020, 2940, 1600, 1495, 1115, 1035, 750 and 695 cm⁻¹.
³⁾I.R. (neat): 3400 (br), 3055, 2940, 1600, 1480, 1280, 1220, 1040, 750 and 705 cm⁻¹.
⁴⁾I.R. (neat):3350 (br), 3050, 2940, 1600, 1480, 1380, 1220, 1040, 870 and 750 cm⁻¹.

What is claimed is:

1. A compound of the formula:

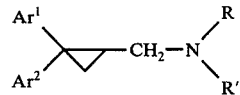

wherein Ar¹ represents a phenyl group having one or more substituents selected from the group consisting of halogen, $C_1$–$C_4$ alkyl, $C_1$–$C_4$ alkoxy and trifluoromethyl, said substituents being present at the o- or m-positions, Ar² represents an unsubstituted phenyl group or a phenyl group substituted with one or more substituents selected from the group consisting of halogen and $C_1$–$C_4$ alkyl, R represents hydrogen, $C_1$–$C_4$ alkyl or $C_2$–$C_4$ hydroxyalkyl and R' represents $C_1$–$C_4$ alkyl or $C_2$–$C_4$ hydroxyalkyl, or a non-toxic salt thereof.

2. The compound according to claim 1, wherein R' is methyl, or a non-toxic salt thereof.

3. The compound according to claim 1, wherein Ar² is an unsubstituted phenyl group or a phenyl group substituted with one or more substituents selected from the group consisting of halogen and $C_1$–$C_4$ alkyl, R is hydrogen or $C_1$–$C_4$ alkyl and R' is $C_1$–$C_4$ alkyl, or a non-toxic salt thereof.

4. The compound according to claim 1, wherein Ar¹ is a phenyl group having one or more substituents selected from the group consisting of halogen, $C_1$–$C_4$ alkyl and $C_1$–$C_4$ alkoxy, said substituents being present at the o- or m-positions, Ar² is an unsubstituted phenyl group or a phenyl group substituted with one or more halogens and R' is $C_2$–$C_4$ hydroxyalkyl, or a non-toxic salt thereof.

5. A pharmaceutical composition comprising as an active ingredient an effective antidepessant or anorexic amount of at least one of the compounds of the formula:

wherein Ar¹ represents a phenyl group having one or more substituents selected from the group consisting of halogen, $C_1$–$C_4$ alkyl, $C_1$–$C_4$ alkoxy and trifluoromethyl, said substituents being present at the o- or m-positions, Ar² represents an unsubstituted phenyl group or a phenyl group substituted with one or more substituents selected from the group consisting of halogen and $C_1$–$C_4$ alkyl, R represents hydrogen, $C_1$–$C_4$ alkyl or $C_2$–$C_4$ hydroxy-alkyl and R' represents $C_1$–$C_4$ alkyl or $C_2$–$C_4$ hydroxyalkyl, or a non-toxic salt thereof, with at least one pharmaceutically acceptable inert carrier or diluent.

6. The compound according to claim 1, wherein Ar¹ is a phenyl group having one or more substituents selected from the group consisting of halogen, methyl, methoxy and trifluoromethyl, said substituents being present at the o- or m-positions, Ar² is an unsubstituted phenyl group or a phenyl group substituted with one or more substituents selected from the group consisting of halogen and methyl, R is hydrogen or methyl and R' is methyl, or a non-toxic salt thereof.

* * * * *